US012731386B2

(12) United States Patent
Zhao et al.

(10) Patent No.: US 12,731,386 B2
(45) Date of Patent: Sep. 8, 2026

(54) METHOD, SYSTEM AND TERMINAL OF CROWDSOURCING ANNOTATION FOR MEDICAL IMAGE DATA BASED ON IMAGE COMPARISON

(71) Applicant: The First Affiliated Hospital of Zhengzhou University, Zhengzhou (CN)

(72) Inventors: Jie Zhao, Zhengzhou (CN); Xianying He, Zhengzhou (CN); Jinming Shi, Zhengzhou (CN); Fangfang Cui, Zhengzhou (CN); Ming Ye, Zhengzhou (CN); Yaoen Lu, Zhengzhou (CN); Lin Wang, Zhengzhou (CN); Jinghong Gao, Zhengzhou (CN); Xiaobing Shi, Zhengzhou (CN); Dongqing Liu, Zhengzhou (CN); Xu Zhang, Zhengzhou (CN)

(73) Assignee: The First Affiliated Hospital of Zhengzhou University, Zhengzhou (CN)

( * ) Notice: Subject to any disclaimer, the term of this patent is extended or adjusted under 35 U.S.C. 154(b) by 493 days.

(21) Appl. No.: 18/213,884

(22) Filed: Jun. 26, 2023

(65) Prior Publication Data

US 2024/0078796 A1 Mar. 7, 2024

(30) Foreign Application Priority Data

Sep. 1, 2022 (CN) ......................... 202211067692.2

(51) Int. Cl.
*G06V 10/778* (2022.01)
*G06V 10/776* (2022.01)
(Continued)

(52) U.S. Cl.
CPC .......... *G06V 10/778* (2022.01); *G06V 10/776* (2022.01); *G06V 20/70* (2022.01); *G16H 30/20* (2018.01); *G16H 30/40* (2018.01)

(58) Field of Classification Search
CPC .... G06V 10/778; G06V 20/70; G06V 10/776; G16H 30/20; G16H 30/40
See application file for complete search history.

(56) References Cited

PUBLICATIONS

Lu, Meng, Research and Implementation of Medical Image Annotation System for Deep Learning, China Excellence Masters' Theses Full-text Database, Medicine & Public Health, May 15, 2021, pp. E060-E017 (Year: 2021).*

(Continued)

*Primary Examiner* — Vu Le
*Assistant Examiner* — Matthew James Bodnark

(57) ABSTRACT

A method of crowdsourcing annotation for medical image data based on image comparison, includes developing an annotation task; acquiring and verifying medical images according to requirements of the annotation task, and performing statistics on the medical images that meet verification standards to obtain an amount of image data acquired; archiving the medical images that meet the verification standards to form a medical image database; setting up annotation rules, and generating annotation schemes and annotation samples according to the requirements of the annotation task and annotation rules; distributing the medical images in the medical image database to multiple crowdsourcing annotation sides, so that each medical image being annotated by the multiple crowdsourcing annotation sides; annotating, by the crowdsourcing annotation sides, the distributed medical images according to the annotation schemes and the annotation examples to form the annotated images; and merging multiple annotated images corresponding to the same medical image.

9 Claims, 6 Drawing Sheets

(51) Int. Cl.
*G06V 20/70* (2022.01)
*G16H 30/20* (2018.01)
*G16H 30/40* (2018.01)

(56) References Cited

PUBLICATIONS

Lu et al, Master's Degree Thesis, Chapter 3 (machine English translation) (Year: 2020).*

* cited by examiner

METHOD, SYSTEM AND TERMINAL OF CROWDSOURCING ANNOTATION FOR MEDICAL IMAGE DATA BASED ON IMAGE COMPARISON

CROSS-REFERENCE TO RELATED APPLICATIONS

The present application claims priority of Chinese Patent Application No. 202211067692.2, filed on Sep. 1, 2022, the entire contents of which are hereby incorporated by reference.

TECHNICAL FIELD

The present disclosure relates to the technical field of data processing, and in particular, relates to a method, a system and a terminal of crowdsourcing annotation for medical image data based on image comparison.

DESCRIPTION OF THE PRIOR ART

Data annotation is the most basic work in the field of artificial intelligence, and high-quality annotated data can effectively improve the performance of artificial intelligence algorithms, and the same is true in the field of medical images.

For data annotation in the field of medical image, the existing annotation methods usually require professionals to manually export the required data from the hospital information system, and then perform preliminary sorting and distribution on the data, and inform the annotators of the required annotation rules, and finally after the annotation is completed, then perform data integration and summary. This method of annotation is less efficient, and can not achieve large-scale medical image annotation, which to a certain extent hinders the development of medical artificial intelligence.

SUMMARY OF THE DISCLOSURE

In view of the shortcomings in the prior art, the technical problem to be solved by the present disclosure is to provide a method, a system and a terminal of crowdsourcing annotation for medical image data based on image comparison, which can effectively improve efficiency and quality of annotation.

In order to solve the above technical problem, the technical solutions taken by the present disclosure are:

a method of crowdsourcing annotation for medical image data based on image comparison, said method comprising:

S10, developing an annotation task;

S20, acquiring and verifying medical images according to requirements of the annotation task, and performing statistics on the medical images that meet verification standards to obtain an amount of image data acquired;

S30, archiving the medical images that meet the verification standards to form a medical image database;

S40, setting up annotation rules, and generating annotation schemes and annotation samples according to the requirements of the annotation task and annotation rules;

S50, distributing the medical images in the medical image database to multiple crowdsourcing annotation sides, so that each medical image being annotated by the multiple crowdsourcing annotation sides;

S60, annotating, by the crowdsourcing annotation sides, the distributed medical images according to the annotation schemes and the annotation examples to form the annotated images; and

S70, merging multiple annotated images corresponding to the same medical image to obtain and archive a final annotation result.

Preferably, the method of crowdsourcing annotation for medical image data based on image comparison further comprises setting up a training module on the crowdsourcing annotation side to train annotators before annotation.

Preferably, the annotation task comprises a disease diagnosis, an image type, and a parameter set annotated this time, wherein an expression of the parameter set is:

para_set={grid_size,coincidence_rate, threshold_value};

where grid_size is a grid size, coincidence_rate is a coincidence rate, and threshold_value is threshold.

Preferably, the step of S70, merging multiple annotated images corresponding to the same medical image to obtain and archive a final annotation specifically comprises:

S701, receiving k annotated images of the same medical image, and cutting each annotated image into a grid-like cell matrix $P_c(m, n)$, $c=1, 2 \ldots, k$ according to the grid size in the expression of the parameter set, where $P_c(m, n)$ represents the cell matrix corresponding to the c-th annotated image, wherein the value of the annotated cell is 1;

S702, superimposing the k annotated images to obtain a repeat matrix;

S703, compressing the repeat matrix based on the threshold to obtain a final repeat matrix so as to delete areas with low repeatability;

S704, calculating an overlap rate of the cell matrix corresponding to each annotated image and the final repeat matrix, and ranking by the overlap rate from high to low;

S705, obtaining the top two cell matrices ranking by the overlap rate, and performing matrix addition on them to calculate a final overlap area;

S706, storing the final overlap area in the database and forming a gold standard after the task is re-verified.

Preferably, the step of S704, calculating an overlap rate of the cell matrix corresponding to each annotated image and the final repeat matrix specifically comprises:

S7041, supposing the cell matrix corresponding to the annotated image is P1(m, n) and the final repeat matrix is P2(m, n) during calculating the overlap rate;

S7042, performing pixel annotation on cell matrices P1(m, n) and P2(m, n) as follows:

setting the annotated cell value to 1 and other unannotated cell values to 0 by pixel;

S7043, performing sampling on the cell matrices P1(m, n) and P2(m, n) after the pixel annotation as follows:

performing x:1 sampling sequentially in the m and n directions on the annotated pixel matrices P1(m, n) and P2(m, n), that is, drawing the last one in every x pixel grids, the sampled matrices are denoted as New_P1(m/x, n/x) and New_P2(m/x, n/x);

and the sizes of the sampled cell matrices are m/x*n/x;

S7044, calculating two-dimensional hashes of New_P1 (m/x, n/x) and New_P2(m/x, n/x) separately, to obtain separately:

a horizontal hash value and a vertical hash value of New_P1(m/x, n/x) and a horizontal hash value and a vertical hash value of New_P2(m/x, n/x);

S7045, calculating a repeatability of the two cell matrices based on the two-dimensional hashes as follows:

comparing the horizontal hash values of New_P1(m/x, n/x) and New_P2(m/x, n/x), to calculate a number of rows with different hash values in the two columns of hash values as;

comparing the vertical hash values of New_P1(m/x, n/x) and New_P2(m/x, n/x), to calculate a number of columns with different hash values in the two rows of hash values as $dif_n$;

an expression for the repeatability is:

$$\text{Repeatability} = \frac{dif_m * dif_n}{m * n}$$

S7046, repeating steps S7041 to S7045, to complete calculations of the overlap rates of the cell matrices corresponding to all the annotated images and the final repeat matrix;

S7047, ranking the overlap rates from high to low based on the overlap rates of the cell matrices corresponding to all the annotation result and the final repeat matrix.

Preferably, in the step S702, an expression of the repeat matrix is:

$$\text{Merge\_P}(m, n) = \Sigma_{c=1}^{k} P_c(m, n) \tag{1}$$

wherein in Equation (1), Merge_P(m, n) represents the repeat matrix;

in the step of S703, an expression of the compression process is:

$$\text{Final\_Merge\_P}(m, n) = \begin{cases} 0, & \text{Merge\_P}(m, n) < \text{ROUND}(\text{coincidence\_rate} * K) \\ 1, & \text{Merge\_P}(m, n) \geq \text{ROUND}(\text{coincidence\_rate} * K) \end{cases} \tag{2}$$

wherein in Equation (2), ROUND(coincidence_rate*K) represents rounded values of the coincidence rate of K images;

Final_Merge_P(m, n) represents the final repeat matrix.

Preferably, in the step of S20, verifying medical images comprises format verification and content verification;

wherein, the format verification is as follows: determining whether a medical image meets the DICOM standard; if yes, the format verification passes, otherwise, the verification does not pass;

the content verification is as follows: determining whether the acquired medical image is consistent with the task issued by an operation and maintenance side; if yes, the content verification passes, otherwise, the verification does not pass;

meeting the verification standard is specifically that both the format check and the content check pass.

Accordingly, the present disclosure also provides a system of crowdsourcing annotation for medical image data based on image comparison, and said system comprises: an operation and maintenance side, a data acquisition side, a central server side and a crowdsourcing annotation side;

the operation and maintenance side is configured to develop an annotation task;

the data acquisition side is configured to dock with a hospital PACS system and to acquire and verify medical images according to requirements of the annotation task, and to perform statistics on the medical images that meet verification standards to obtain an amount of image data acquired;

the central server side is configured to archive the medical images that meet the verification standards to form a medical image database;

to set up annotation rules, and generate annotation schemes and annotation samples according to the requirements of the annotation task and annotation rules;

to distribute the medical images in the medical image database to multiple crowdsourcing annotation sides, so that each medical image being annotated by the multiple crowdsourcing annotation sides; and to receive annotation results from the crowdsourcing annotation sides and to merge multiple annotated images corresponding to the same medical image to obtain and archive a final annotation result;

the crowdsourcing annotation side annotates the distributed medical images according to the annotation schemes and the annotation examples to form the annotated images.

Accordingly, the present disclosure also provides a terminal comprises:

a memory, configured to store computer programs;

a controller, configured to implement the above method of crowdsourcing annotation for medical image data based on image comparison when executing the computer programs.

The beneficial effects of the present disclosure are as follows:

According to the method, the system and the terminal of crowdsourcing annotation for medical image data based on image comparison provided by the present disclosure, annotation is performed in a crowdsourcing manner, which maximizes the annotation speed. By merging multiple annotated images to obtain and archive the final annotation result, a high accuracy annotation result can be automatically obtained, reducing workload while ensuring accuracy, with strong practicality.

Figure 1:
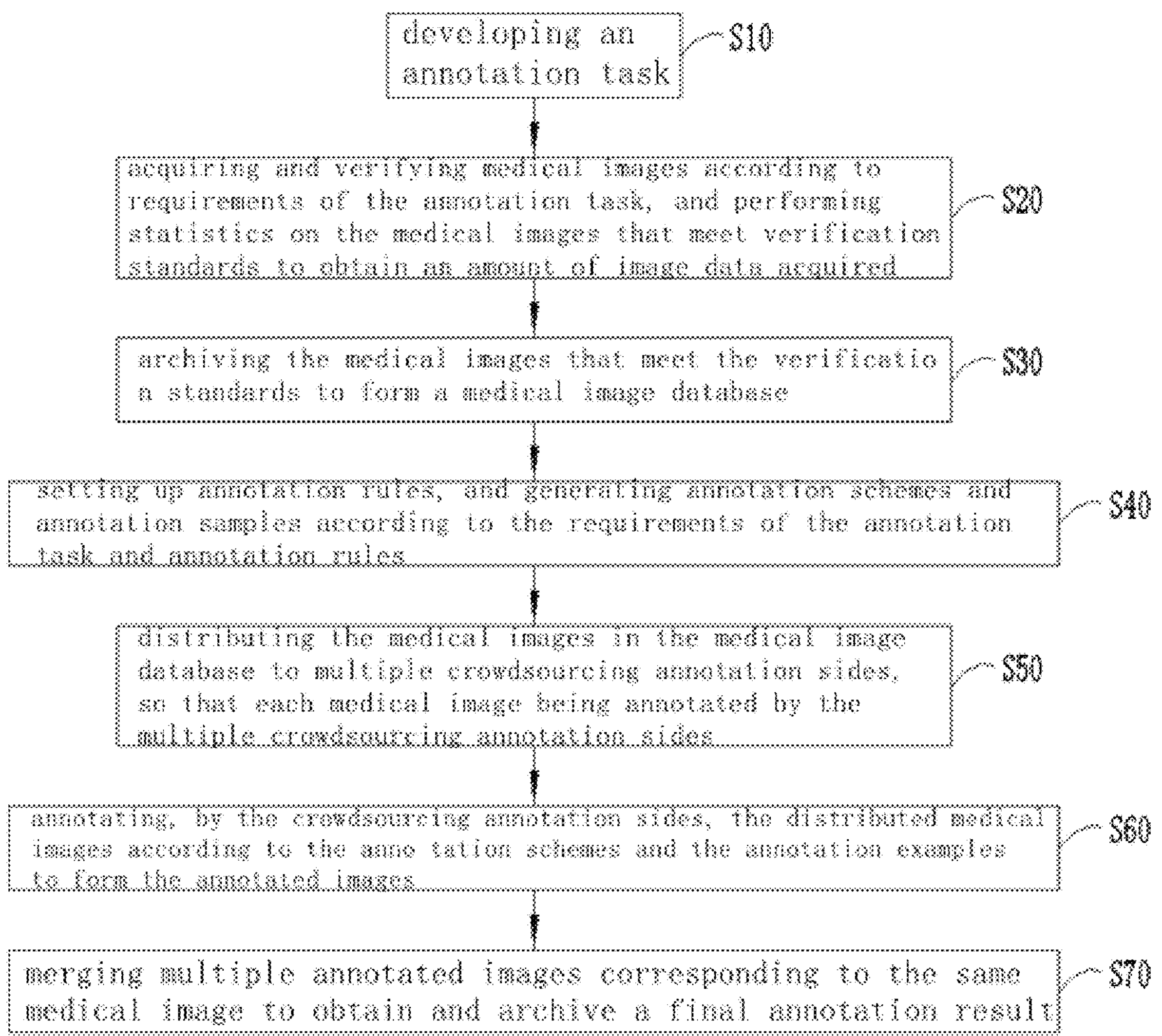
FIG. 1 is a flow chart of the method of crowdsourcing annotation for medical image data based on image comparison provided by Embodiment 1 according to the present disclosure.

In the drawings, 10: Operation and maintenance side; 20: Data acquisition side; 30: Central server side; and 40: Crowdsourcing annotation side.

DESCRIPTION OF EMBODIMENTS

In order to make the object, technical solutions and advantages of embodiments of the present disclosure clearer, the technical solutions in the embodiments of the present disclosure will be clearly and completely described in conjunction with drawings of the embodiments of the present disclosure. Obviously, the described embodiments are only a part of the embodiments of the present disclosure rather than all embodiments. Based on the embodiments in the present disclosure, all other embodiments obtained by ordinary people skilled in the art without making creative labor, fall within the scope of the protection of the present disclosure.

Secondly, the present disclosure is described in detail in conjunction with schematic diagrams, in detailing embodiments of the present disclosure, for ease of illustration, the profile view indicating the device structure will not be locally enlarged according to the general proportion, and the schematic diagrams are only examples, which should not limit the scope of protection of the present disclosure.

In addition, the actual production, three-dimensional spatial dimensions of length, width and depth should be included.

The following details an embodiment of the present disclosure in conjunction with the drawings.

Embodiment 1

As shown in FIG. 1, the method of crowdsourcing annotation for medical image data based on image comparison comprises:

S10, developing an annotation task;

S20, acquiring and verifying medical images according to requirements of the annotation task, and performing statistics on the medical images that meet verification standards to obtain an amount of image data acquired;

S30, archiving the medical images that meet the verification standards to form a medical image database;

S40, setting up annotation rules, and generating annotation schemes and annotation samples according to the requirements of the annotation task and annotation rules;

S50, distributing the medical images in the medical image database to multiple crowdsourcing annotation sides, so that each medical image being annotated by the multiple crowdsourcing annotation sides;

S60, annotating, by the crowdsourcing annotation sides, the distributed medical images according to the annotation schemes and the annotation examples to form the annotated images; and S70, merging multiple annotated images corresponding to the same medical image to obtain and archive a final annotation result.

In particular, in this embodiment, the annotation task comprises a disease diagnosis, an image type, and a parameter set annotated this time; the expression of the parameter set is:

para_set={grid_size,coincidence_rate, threshold_value};

where grid_size is a grid size, coincidence_rate is a coincidence rate, and threshold_value is threshold.

Further, in the step of S20, verifying medical images comprises format verification and content verification;

wherein, the format verification is as follows: determining whether a medical image meets the DICOM standard; if yes, the format verification passes, otherwise, the verification does not pass;

the content verification is as follows: determining whether the acquired medical image is consistent with the task issued by an operation and maintenance side; if yes, the content verification passes, otherwise, the verification does not pass;

meeting the verification standard is specifically that both the format check and the content check pass.

In this embodiment, the step of S40, setting up annotation rules, and generating annotation schemes and annotation samples according to the requirements of the annotation task and annotation rules; wherein the annotation schemes comprise:

scheme description document, which is used to describe the specific contents that need to be annotated this time, annotation standards, and precautions;

the gold standards for medical image annotation, which can be the gold standards of the medical image annotation annotated by multiple experts this time, as a sample annotation for the reference of crowdsourcing annotators.

In this embodiment, the step of S50, distributing the medical images in the medical image database to multiple crowdsourcing annotation sides, so that each medical image being annotated by the multiple crowdsourcing annotation sides, specifically comprises:

S501, querying an assignment list of historical annotation tasks, selecting a medical image data in the dataset, and checking whether the medical image data has been crowdsourcing annotated: if yes, selecting the next medical image data; if no, assigning the medical image data to the crowdsourcing annotation side for annotation; and sending the annotation result to the central server side after the crowdsourcing annotation side completing the annotation of the medical image data;

S502, repeating step S501 until all medical image data in the dataset are annotated;

S503, assigning the annotation tasks of the dataset to multiple crowdsourced annotation sides according to the method of step S501 to step S502, until each data in the dataset is annotated by several crowdsourcing annotation sides.

Further comprises setting up a training module on the crowdsourcing annotation side to train annotators before annotation.

The present disclosure also provides a system of crowdsourcing annotation for medical image data based on image comparison.

Figure 2:
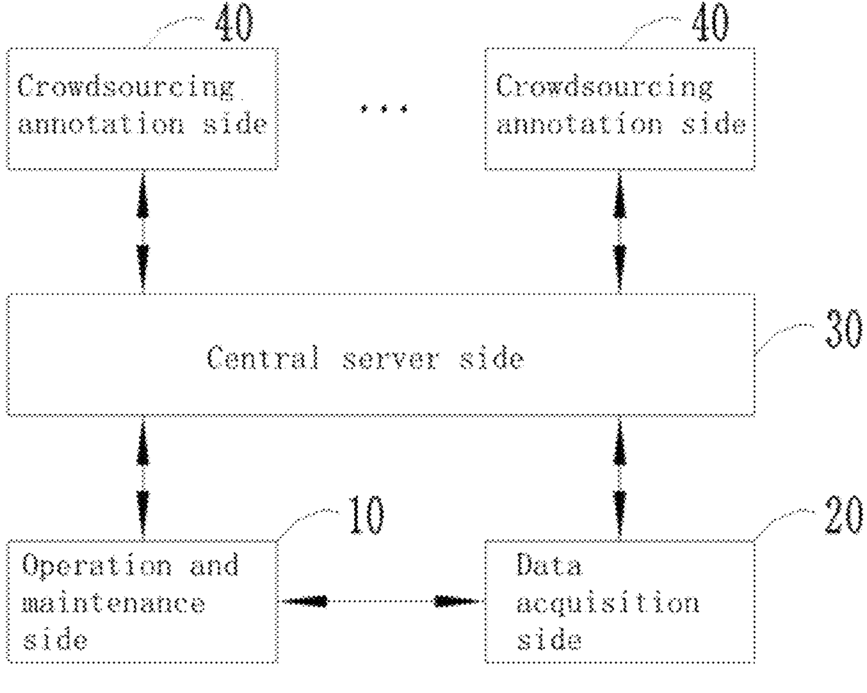
FIG. 2 is a diagram of the system of crowdsourcing annotation for medical image data based on image comparison provided by Embodiment 1 according to the present disclosure.

As shown in FIG. 2, a system of crowdsourcing annotation for medical image data based on image comparison comprises: an operation and maintenance side 10, a data acquisition side 20, a central server side 30 and a crowdsourcing annotation side 40;

the operation and maintenance side 10 is configured to develop an annotation task;

the data acquisition side 20 is configured to dock with a hospital PACS system and to acquire and verify medical images according to requirements of the annotation task, and to perform statistics on the medical images that meet verification standards to obtain an amount of image data acquired;

the central server side 30 is configured to archive the medical images that meet the verification standards to form a medical image database;

to set up annotation rules, and generate annotation schemes and annotation samples according to the requirements of the annotation task and annotation rules;

to distribute the medical images in the medical image database to multiple crowdsourcing annotation sides 40, so that each medical image being annotated by the multiple crowdsourcing annotation sides 40; and to receive annotation results from the crowdsourcing annotation sides 40 and to merge multiple annotated images corresponding to the same medical image to obtain and archive a final annotation result;

the crowdsourcing annotation side 40 annotates the distributed medical images according to the annotation schemes and the annotation examples to form the annotated images.

In this embodiment, the hospital PACS system refers to image archiving and communication system.

In this embodiment, the data is annotated by crowdsourcing, and a crowdsourcing annotation side has functions such as training before participating in annotation, participating in annotation, and result feedback.

Training before annotation: crowdsourcing annotation has the characteristics of fast speed and low cost, etc.; However if the levels of crowdsourced annotators are uneven, it will directly affect the final annotation results of medical image data; Therefore, before participating in the annotation, it is necessary to assess and identify the level of the annotator, and customize different levels of personalized training schemes according to its assessment performance, and when annotating different types of data, the system will push relevant annotation manuals and schemes to improve the accuracy of annotation.

Participating in annotation: that is, the annotation of medical image data is started in a crowdsourcing manner; Crowdsourcing annotation is an important feature of the present disclosure; Compared to outsourcing annotation, crowdsourcing annotation has the characteristics of fast annotation speed, low cost and so on; Any certified and trained medical staff can participate in the annotation work, and by giving corresponding remuneration or allowing the use of some data and other incentive measures to mobilize the enthusiasm of medical staff.

Result feedback: after the annotation is completed, the annotation results of the crowdsourcing participant can be fed back to the operation and maintenance side; The operation and maintenance side records the annotation results and associate them with the participating annotators, which can be used for scoring the participating annotators and subsequent performance appraisal management, etc.

In this embodiment, by deploying the data acquisition side and docking with the hospital PACS system, the acquisition of medical images to be annotated is realized, and at the same time, through verification and statistics, the screening and preliminary sorting of data is completed, reducing the workload of manual screening of data; At the same time, during the annotation, the annotation is performed by crowdsourcing to maximize the annotation rate.

In addition, the crowdsourcing annotation side in the present application can be set up with a training module to certify the participants in the crowdsourcing annotation and improve the quality of the annotation. Through the teaching and training of the crowdsourcing annotators, annotations with different granularities can be completed. The teaching of crowdsourced annotation participants can also be realized through machine learning algorithms, and personalized training can be achieved for each participant.

According to the method, the system and the terminal of crowdsourcing annotation for medical image data based on image comparison provided by the present disclosure, annotation is performed in a crowdsourcing manner, which maximizes the annotation speed. By merging multiple annotated images to obtain and archive the final annotation result, a high accuracy annotation result can be automatically obtained, reducing workload while ensuring accuracy, with strong practicality.

Embodiment 2

In this embodiment, assuming that for one medical image, a total of K annotators have performed annotation this time, that is, k annotated images with different annotation results are obtained, and the specific process of merging multiple annotated images is as follows.

Figure 3:
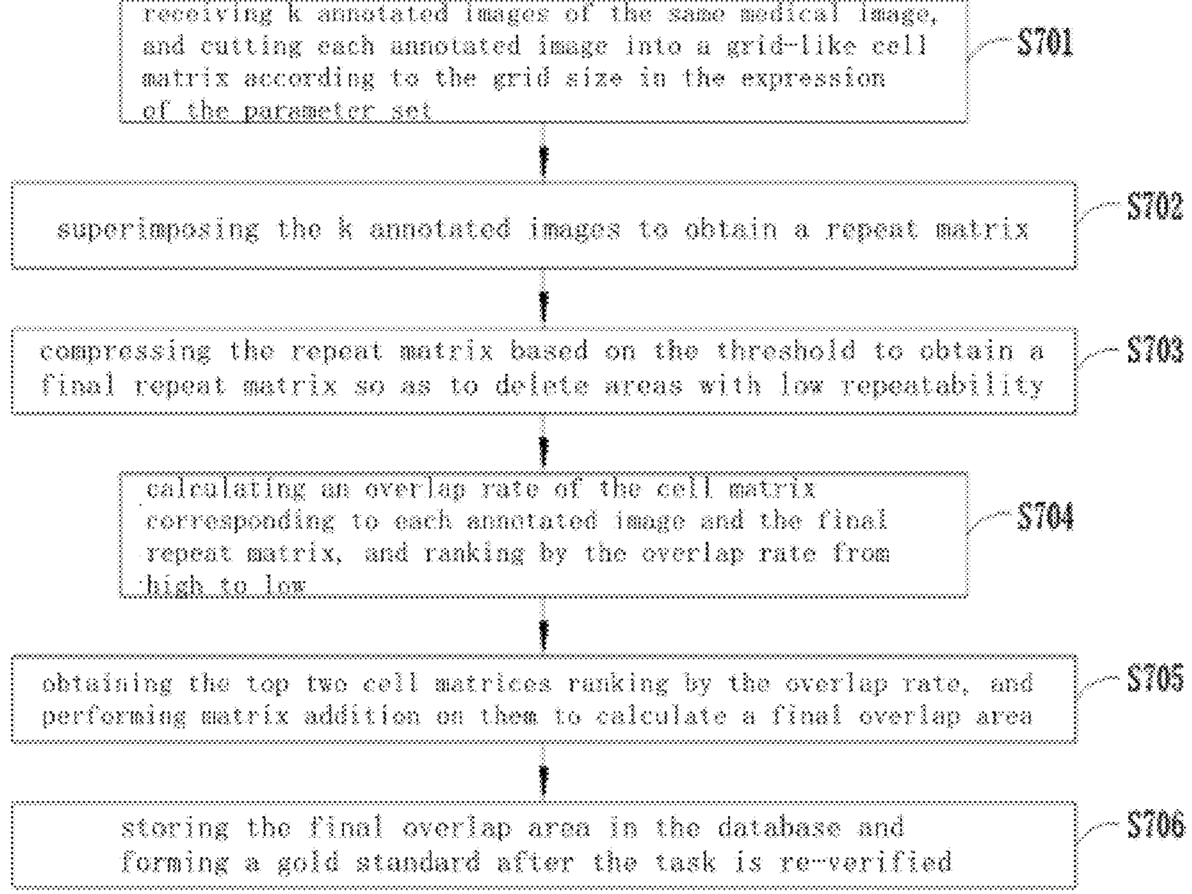
FIG. 3 is a flow chart of step S70 in the method of crowdsourcing annotation for medical image data based on image comparison provided by Embodiment 2 according to the present disclosure.
Figure 4:
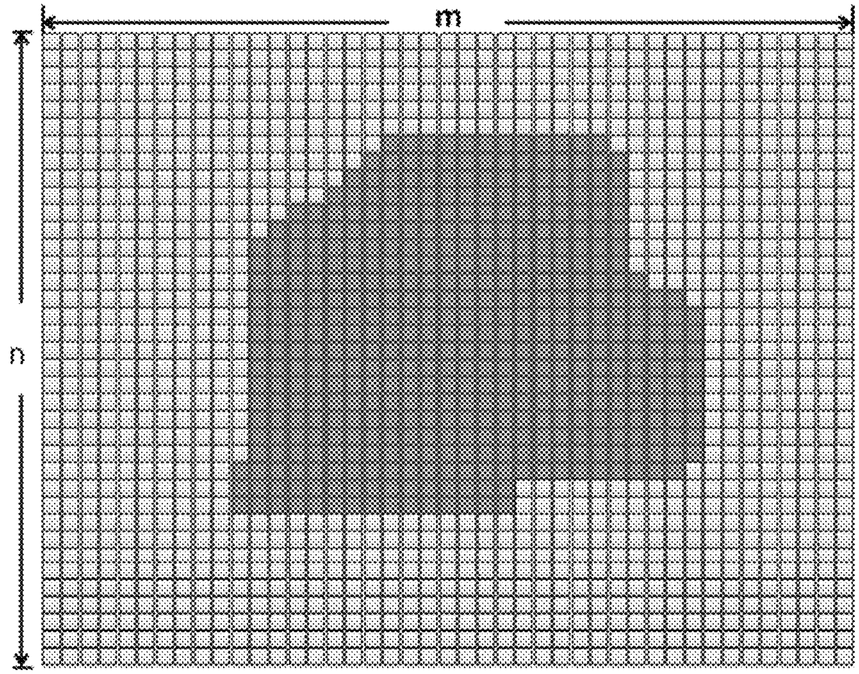
FIG. 4 is a diagram of the cell matrix in the method of crowdsourcing annotation for medical image data based on image comparison provided by Embodiment 2 according to the present disclosure.

As shown in FIG. 3, in the method of crowdsourcing annotation for medical image data based on image comparison, the step of S70, merging multiple annotated images corresponding to the same medical image to obtain and archive a final result specifically comprises:

S701, receiving k annotated images of the same medical image, and cutting each annotated image into a grid-like cell matrix $P_c(m, n)$, c=1, 2 . . . , k according to the grid size in the expression of the parameter set, where $P_c(m, n)$ represents the cell matrix corresponding to the c-th annotated image, wherein the value of the annotated cell is 1;

In this step, for each annotation result:

Firstly, according to the single grid size specified in the first parameter grid_size in the parameter set para_set, each annotation result is divided into a grid-like cell matrix P(m, n);

Then, the value of the cells covered by the area annotated by annotator are set to 1; As shown in FIG. 4, the area with dark grayscale in FIG. 4 is the area annotated by an annotator, and the cells in the area with dark grayscale have a corresponding matrix value of 1.

S702, superimposing the k annotated images to obtain a repeat matrix; Specifically, the expression of the repeat matrix is:

$$\text{Merge\_P}(m, n) = \Sigma_{c=1}^{k} P_c(m, n) \tag{1}$$

wherein in Equation (1), Merge_P(m, n) represents the repeat matrix;

In this step, Merge_P(m, n) comprises a number of overlaps for each cell (i.e., the number of times each cell is annotated).

S703, compressing the repeat matrix based on the threshold to obtain a final repeat matrix so as to delete areas with low repeatability; Specifically, the expression of the compression processing is:

$$\text{Final\_Merge\_P}(m, n) = \begin{cases} 0, \text{Merge\_P}(m, n) < \text{ROUND}(\text{coincidence\_rate} * K) \\ 1, \text{Merge\_P}(m, n) \geq \text{ROUND}(\text{coincidence\_rate} * K) \end{cases} \quad (2)$$

wherein in Equation (2), ROUND(coincidence_rate*K) represents rounded values of the coincidence rate of K images;

Final_Merge_P(m, n) represents the final repeat matrix;

In this step, due to the large repeat matrix, the threshold for screening can be calculated based on the second parameter coincidence_rate i.e., the coincidence rate in the parameter set para_set.

S704, calculating an overlap rate of the cell matrix corresponding to each annotated image and the final repeat matrix, and ranking by the overlap rate from high to low;

S705, obtaining the top two cell matrices ranking by the overlap rate, and performing matrix addition on them to calculate a final overlap area;

S706, storing the final overlap area in the database and forming a gold standard after the task is re-verified.

Figure 5:
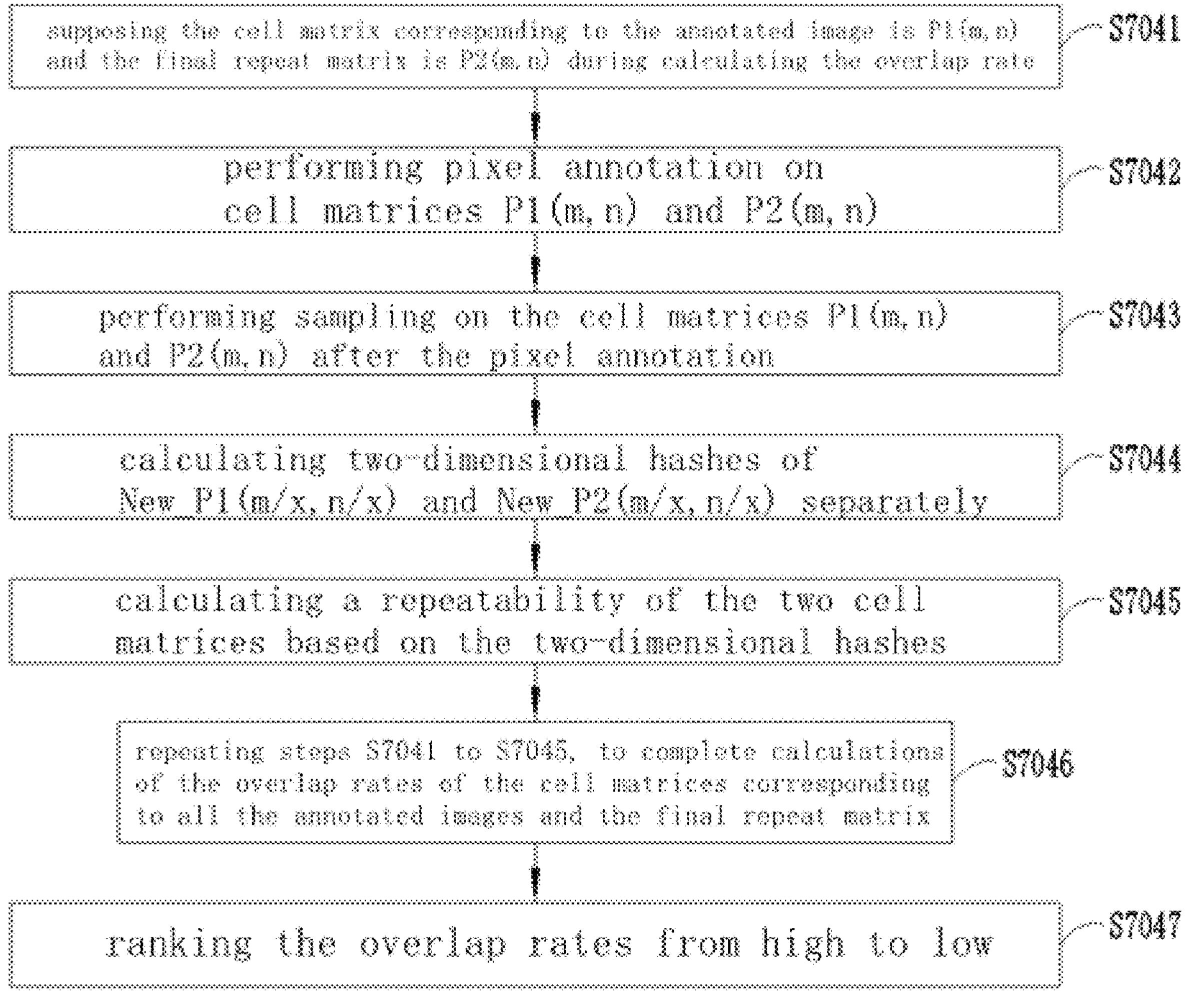
FIG. 5 is a flow chart of step S704 in the method of crowdsourcing annotation for medical image data based on image comparison provided by Embodiment 2 according to the present disclosure.

In this embodiment, considering that medical image files are usually large, when comparing in pixels, the demand for computing resources is high, and the comparison time is long. In order to quickly calculate the overlap rate between the two annotated images, in the present application, an image overlap rate calculation method based on image sampling and two-dimensional hash is designed, as follows:

As shown in FIG. 5, in the step of S704, calculating an overlap rate of the cell matrix corresponding to each annotated image and the final repeat matrix specifically comprises:

S7041, supposing the cell matrix corresponding to the annotated image is P1(m, n) and the final repeat matrix is P2(m, n) during calculating the overlap rate;

S7042, performing pixel annotation on cell matrices P1(m, n) and P2(m, n) as follows:

setting the annotated cell value to 1 and other unannotated cell values to 0 by pixel;

S7043, performing sampling on the cell matrices P1(m, n) and P2(m, n) after the pixel annotation as follows:

performing x:1 sampling sequentially in the m and n directions on the annotated pixel matrices P1(m, n) and P2(m, n), that is, drawing the last one in every x pixel grids, the sampled matrices are denoted as New_P1(m/x, n/x) and New_P2(m/x, n/x);

and the sizes of the sampled cell matrices are m/x*n/x;

S7044, calculating two-dimensional hashes of New_P1 (m/x, n/x) and New_P2(m/x, n/x) separately, to obtain separately:

a horizontal hash value and a vertical hash value of New_P1(m/x, n/x) and a horizontal hash value and a vertical hash value of New_P2(m/x, n/x);

S7045, calculating a repeatability of the two cell matrices based on the two-dimensional hashes as follows:

comparing the horizontal hash values of New_P1(m/x, n/x) and New_P2(m/x, n/x), to calculate a number of rows with different hash values in the two columns of hash values as;

comparing the vertical hash values of New_P1(m/x, n/x) and New_P2(m/x, n/x), to calculate a number of columns with different hash values in the two rows of hash values as $dif_n$;

an expression for the repeatability is:

$$\text{Repeatability} = \frac{dif_m * dif_n}{m * n}$$

S7046, repeating steps S7041 to S7045, to complete calculations of the overlap rates of the cell matrices corresponding to all the annotated images and the final repeat matrix;

S7047, ranking the overlap rates from high to low based on the overlap rates of the cell matrices corresponding to all the annotation result and the final repeat matrix.

Specifically, during x:1 sampling in the m and n directions, the value of x is preferably 10.

Taking the value 10 as an example, after sampling, the matrix is New_P1(m/10,n/10) and New_P2(m/10,n/10), and its size is m/10*n/10, reducing the size of the original image by 100 times.

Figure 6:
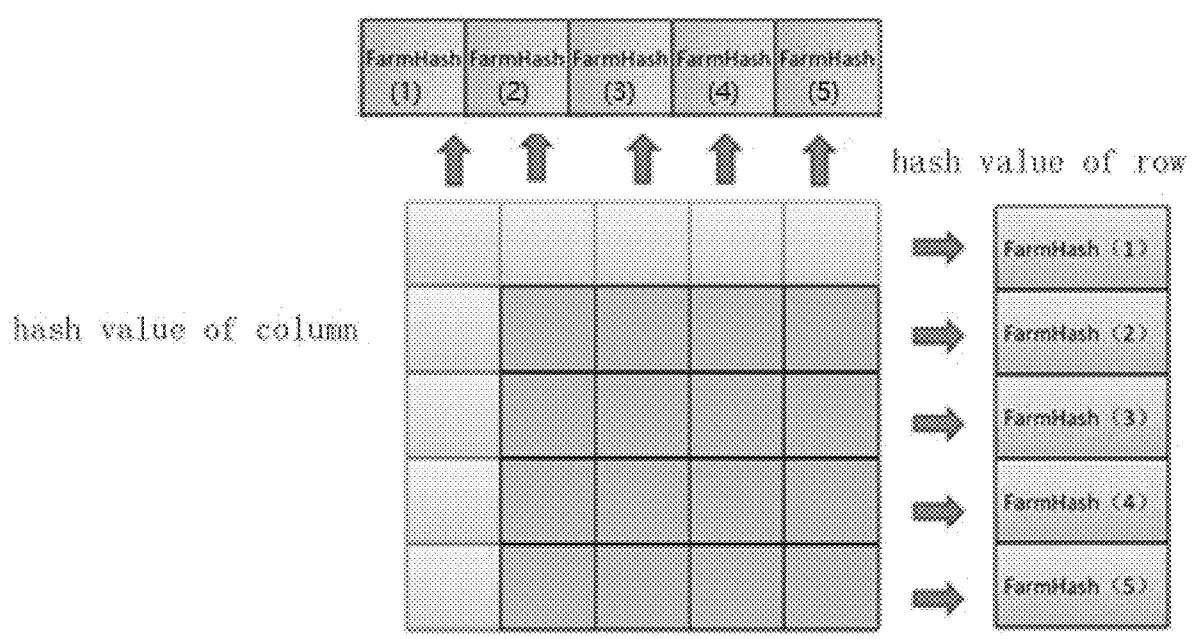
FIG. 6 is a schematic diagram of the calculation of the two-dimensional hash in the method of crowdsourcing annotation for medical image data based on image comparison provided by Embodiment 2 according to the present disclosure.

Further, as shown in FIG. 6, for New_P1(m/10,n/10) and New_P2(m/10,n/10), using the FarmHash function to calculate the hash value of each horizontal row and each vertical column respectively. The FarmHash function takes the 0-1 matrix of the row or column as input, and outputs a 64-bit unique hash value, so as to obtain a vertical hash feature with size [1, m/10] and a horizontal hash feature with size [1, n/10].

The present disclosure also provides a storage device in which a plurality of instructions are stored, the instructions are suitable for being loaded by a processor to execute the method of crowdsourced annotation for medical image data based on image alignment as described above.

The storage device may be a computer-readable storage medium, which may include: ROM, RAM, disk or optical disk, etc.

The present disclosure also provides a terminal comprises:

a processor, suitable for implementing each instruction; and a storage device, suitable for storing a plurality of instructions, and the instructions are suitable for being loaded by the processor to execute the method of crowdsourcing annotation for medical image data based on image comparison as described above.

The terminal may be a desktop computer, a laptop, etc., which may be realized by software and/or hardware.

In the description of the present specification, the terms "one embodiment", "some embodiments", "examples", "specific examples", or "some examples" are referred to in conjunction with the specific features, structures, materials or characteristics described in conjunction with the embodiment or example described in at least one embodiment or example of the present disclosure.

In the present specification, the schematic expression of the above terms does not have to refer to the same embodiment or example.

Further, the specific features, structures, materials or characteristics described may be combined in any one or more embodiments or examples in a suitable manner.

Further, without contradictory, those skilled in the art may combine and combine different embodiments or examples described in the present specification and the characteristics of different embodiments or examples.

In the above embodiments, the description of each embodiment has its own emphasis, and the part not described in detail in one embodiment may refer to the relevant description of other embodiments.

It is understood that the above methods, devices and related features in the system can be cross-referenced.

Further, the "first", "second", etc. in the above embodiments are used to distinguish each embodiment, and do not represent the advantages and disadvantages of each embodiment Those skilled in the art can clearly understand that for the convenience and conciseness of the description, the specific working process of the system and module described above may refer to the corresponding process in the embodiment of the aforementioned method, which will not be repeated herein.

The algorithms and displays provided herein are not intrinsically related to any particular computer, virtual system, or other device.

Various universal systems can also be used with teachings based here.

According to the above description, the structure required to construct such a device is obvious.

Further, the present disclosure does not target any particular programming language.

It should be understood that the content of the present disclosure described herein may be implemented in various programming languages, and the description of the above for a particular language is intended to disclose the best embodiment of the present disclosure.

Finally, it should be noted that the above embodiments are only used to illustrate the technical solution of the present disclosure, and are not limited thereto; Although the present disclosure is described in detail with reference to the foregoing embodiments, those of ordinary skill in the art should understand: they may still modify the technical solutions described in the foregoing embodiments, or replace some or all of the technical features equivalently; And these modifications or replacements, do not make the essence of the corresponding technical solution out of the scope of the technical solution of each embodiment of the present disclosure.

The invention claimed is:

1. A method of crowdsourcing annotation for medical image data based on image comparison, said method comprising steps of:

S10, developing an annotation task;

S20, acquiring and verifying medical images according to requirements of the annotation task, and performing statistics on the medical images that meet verification standards to obtain an amount of image data acquired;

S30, archiving the medical images that meet the verification standards to form a medical image database;

S40, setting up annotation rules, and generating annotation schemes and annotation samples according to the requirements of the annotation task and annotation rules;

S50, distributing the medical images in the medical image database to multiple crowdsourcing annotation sides, so that each medical image being annotated by the multiple crowdsourcing annotation sides;

S60, annotating, by the crowdsourcing annotation sides, the distributed medical images according to the annotation schemes and the annotation examples to form the annotated images; and S70, merging multiple annotated images corresponding to the same medical image to obtain and archive a final annotation result, wherein the annotation task comprises a disease diagnosis, an image type, and a parameter set annotated this time, wherein an expression of the parameter set is: para_set={grid_size, coincidence_rate, threshold_value};

where grid_size is a grid size, coincidence_rate is a coincidence rate, and threshold_value is threshold.

2. The method of crowdsourcing annotation for medical image data based on image comparison according to claim 1, wherein said method further comprises: setting up a training module on the crowdsourcing annotation side to train annotators before annotation.

3. The method of crowdsourcing annotation for medical image data based on image comparison according to claim 1, wherein in the step of S20, verifying medical images comprises format verification and content verification;

wherein, the format verification is as follows: determining whether a medical image meets the DICOM standard; if yes, the format verification passes, otherwise, the verification does not pass; the content verification is as follows: determining whether the acquired medical image is consistent with the task issued by an operation and maintenance side; if yes, the content verification passes, otherwise, the verification does not pass;

meeting the verification standard is specifically that both the format check and the content check pass.

4. A terminal, comprising:

a memory, configured to store computer programs;

a controller, configured to implement the method of crowdsourcing annotation for medical image data based on image comparison according to claim 1 when executing the computer programs.

5. A method of crowdsourcing annotation for medical image data based on image comparison, said method comprising steps of:

S10, developing an annotation task;

S20, acquiring and verifying medical images according to requirements of the annotation task, and performing statistics on the medical images that meet verification standards to obtain an amount of image data acquired;

S30, archiving the medical images that meet the verification standards to form a medical image database;

S40, setting up annotation rules, and generating annotation schemes and annotation samples according to the requirements of the annotation task and annotation rules;

S50, distributing the medical images in the medical image database to multiple crowdsourcing annotation sides, so that each medical image being annotated by the multiple crowdsourcing annotation sides;

S60, annotating, by the crowdsourcing annotation sides, the distributed medical images according to the annotation schemes and the annotation examples to form the annotated images; and S70, merging multiple annotated images corresponding to the same medical image to obtain and archive a final annotation result, wherein the annotation task comprises a disease diagnosis, an image type, and a parameter set annotated this time, wherein an expression of the parameter set is: para set={grid size, coincidence rate, threshold_value};

where grid size is a grid size, coincidence rate is a coincidence rate, and threshold_value is threshold, wherein in the step of S70, merging multiple annotated images corresponding to the same medical image to obtain and archive a final result specifically comprises:

S701, receiving k annotated images of the same medical image, and cutting each annotated image into a grid-like cell matrix $P_c(m, n)$, c=1, 2, . . . , k according to the grid size in the expression of the parameter set, where $P_c(m, n)$ represents the cell matrix corresponding to the c-th annotated image, wherein the value of the annotated cell is 1;

S702, superimposing the k annotated images to obtain a repeat matrix;

S703, compressing the repeat matrix based on the threshold to obtain a final repeat matrix so as to delete areas with low repeatability;

S704, calculating an overlap rate of the cell matrix corresponding to each annotated image and the final repeat matrix, and ranking by the overlap rate from high to low;

S705, obtaining the top two cell matrices ranking by the overlap rate, and performing matrix addition on them to calculate a final overlap area;

S706, storing the final overlap area in the database and forming a gold standard after the task is re-verified.

6. The method of crowdsourcing annotation for medical image data based on image comparison according to claim 5, wherein in the step of S704, calculating an overlap rate of the cell matrix corresponding to each annotated image and the final repeat matrix specifically comprises:

S7041, supposing the cell matrix corresponding to the annotated image is P1(m, n) and the final repeat matrix is P2(m, n) during calculating the overlap rate;

S7042, performing pixel annotation on cell matrices P1(m, n) and P2(m, n) as follows:

setting the annotated cell value to 1 and other unannotated cell values to 0 by pixel;

S7043, performing sampling on the cell matrices P1(m, n) and P2(m, n) after the pixel annotation as follows:

performing x:1 sampling sequentially in the m and n directions on the annotated pixel matrices P1(m, n) and PZ (m, n), that is, drawing the last one in every x pixel grids, the sampled matrices are denoted as New_P1(m/x, n/x) and New_P2(m/x, n/x);

and the sizes of the sampled cell matrices are m/x*n/x;

S7044, calculating two-dimensional hashes of New_P1 (m/x, n/x) and

New_P2(m/x, n/x) separately, to obtain separately:

a horizontal hash value and a vertical hash value of New_P1(m/x, n/x) and a horizontal hash value and a vertical hash value of New_P2(m/x, n/x);

S7045, calculating a repeatability of the two cell matrices based on the two-dimensional hashes as follows:

comparing the horizontal hash values of New_P1(m/x, n/x) and

New_P2(m/x, n/x), to calculate a number of rows with different hash values in the two columns of hash values as;

comparing the vertical hash values of New_P1(m/x, n/x) and

New_P2(m/x, n/x), to calculate a number of columns with different hash values in the two rows of hash values as $dif_n$;

an expression for the repeatability is:

$$\text{Repeatability} = \frac{dif_m * dif_n}{m * n}$$

S7046, repeating steps S7041 to S7045, to complete calculations of the overlap rates of the cell matrices corresponding to all the annotated images and the final repeat matrix;

S7047, ranking the overlap rates from high to low based on the overlap rates of the cell matrices corresponding to all the annotation result and the final repeat matrix.

7. The method of crowdsourcing annotation for medical image data based on image comparison according to claim 5, wherein in the step of S702, an expression of the repeat matrix is:

$$\text{Merge\_P}(m, n) = \Sigma_{c=1}^{k} P_c(m, n) \quad (1)$$

wherein in Equation (1), Merge_P (m, n) represents the repeat matrix;

in the step of S703, an expression of the compression process is:

$$\text{Final\_Merge\_P}(m, n) = \begin{cases} 0, \text{Merge\_P}(m, n) < \text{ROUND}(\text{coincidence\_rate} * K) \\ 1, \text{Merge\_P}(m, n) \geq \text{ROUND}(\text{coincidence\_rate} * K) \end{cases} \quad (2)$$

wherein in Equation (2), ROUND (coincidence_rate*K) represents rounded values of the coincidence rate of K images;

Final_Merge_P (m, n) represents the final repeat matrix.

8. A terminal, comprising:

a memory, configured to store computer programs;

a controller, configured to implement the method of crowdsourcing annotation for medical image data based on image comparison according to claim 5 when executing the computer programs.

9. The method of crowdsourcing annotation for medical image data based on image comparison according to claim 5, wherein said method further comprises:

setting up a training module on the crowdsourcing annotation side to train annotators before annotation.

* * * * *